United States Patent [19]

Tessier et al.

[11] Patent Number: 4,879,302
[45] Date of Patent: Nov. 7, 1989

[54] CERTAIN OXIMINO-CYCLOPROPANE CARBOXYLATES HAVING INSECTICIDAL ACTIVITY

[75] Inventors: Jean Tessier, Vincennes; Jean-Pierre Demoute, Montreuil-sour-Bois; Joseph Cadiergue, Aulnay sous Bois, all of France

[73] Assignee: Roussel Vclaf, Romainville, France

[21] Appl. No.: 114,534

[22] Filed: Oct. 29, 1987

[30] Foreign Application Priority Data

Oct. 30, 1986 [FR] France ................. 86-15124

[51] Int. Cl.$^4$ ............... C07C 69/743; C07C 121/48; A01N 43/40; A01N 53/00
[52] U.S. Cl. .................... 514/351; 514/521; 514/531; 546/300; 558/407; 560/124
[58] Field of Search ............ 558/407; 560/124; 546/300; 514/521, 531, 351

[56] References Cited

U.S. PATENT DOCUMENTS 4,439,446 10/1987 Soloway ............... 514/521
4,622,337 11/1986 Elliott et al. ............ 514/461

*Primary Examiner*—Alan L. Rotman
*Attorney, Agent, or Firm*—Bierman & Muserlian

[57] ABSTRACT

All possible stereoisomeric forms and mixtures thereof of a compound of the formula

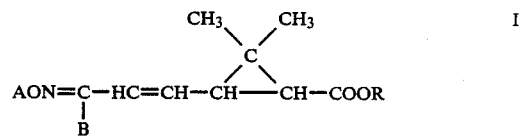

wherein A is selected from the group consisting of hydrogen, optionally unsaturated alkyl and haloalkyl of 1 to 18 carbon atoms, optionally substituted with aryl or a heterocyclic and optionally interrupted by —O— or —S—, optionally unsaturated cycloalkyl of 3 to 18 carbon atoms, aryl of 6 to 14 carbon atoms and heterocyclic, B is selected from the group consisting of hydrogen, alkyl of 1 to 18 carbon atoms optionally interrupted by —S— or —O— and optionally substituted with at least one member of the group consisting of halogen, —OH, alkoxy of 1 to 8 carbon atoms, —SH, thioalkoxy of 1 to 8 carbon atoms, —NO$_2$ and —CN and R is selected from the group consisting of optionally unsaturated alkyl of 1 to 18 carbon atoms and residue of an alcohol used in the synthesis of pyrethrinoid esters having pesticidal activity.

18 Claims, No Drawings

CERTAIN OXIMINO-CYCLOPROPANE CARBOXYLATES HAVING INSECTICIDAL ACTIVITY

STATE OF THE ART

Chemical Abstracts, Vol. 87, No. 1, p. 108, No. 1193Y describes related cyclopropane carboxylates.

OBJECTS OF THE INVENTION

It is an object of the invention to provide the novel compounds of formula I and a process for their preparations.

It is another object of the invention to provide novel pesticidal compositions and a novel method of combatting pests.

These and other objects and advantages of the invention will become obvious from the following detailed description.

THE INVENTION

The novel compounds of the invention are all possible stereoisomeric forms and mixtures thereof of a compound of the formula

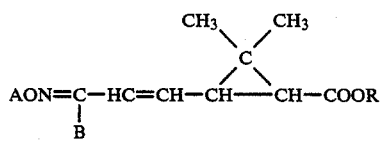

I wherein A is selected from the group consisting of hydrogen, optionally unsaturated alkyl and haloalkyl of 1 to 18 carbon atoms, optionally substituted with aryl or a heterocyclic and optionally interrupted by —O— or —S—, optionally unsaturated cycloalkyl of 3 to 18 carbon atoms, aryl of 6 to 14 carbon atoms and heterocyclic, B is selected from the group consisting of hydrogen, alkyl of 1 to 18 carbon atoms optionally interrupted by —S— or —O— and optionally substituted with at least one member of the group consisting of halogen, —OH, alkoxy of 1 to 8 carbon atoms, —SH, thioalkoxy of 1 to 8 carbon atoms, —$NO_2$ and —CN and R is selected from the group consisting of optionally unsaturated alkyl of 1 to 18 carbon atoms and residue of an alcohol used in the synthesis of pyrethrinoid esters.

When A or B is saturated alkyl, it is preferably methyl, ethyl, n-propyl, isopropyl, n-butyl, sec-butyl, tert-butyl, n-pentyl or n-hexyl. When A or B is unsaturated alkyl, it is preferably alkenyl such as vinyl or 1,1-dimethyl-allyl or alkynyl such as ethynyl or propynyl. When A or B are alkyl substituted by halogen, they are preferably alkyl substituted by fluorine, chlorine or bromine.

When A is alkyl substituted by aryl radical, the aryl is preferably phenyl. When A is alkyl substituted by a heterocyclic, the heterocyclic is preferably furyl, pyranyl, benzofuranyl, oxazolyl, thienyl, thiazolyl, pyridinyl or pyrimidinyl. When B is alkyl substituted by alkoxy, the alkoxy is preferably methoxy or ethoxy.

When R is alkyl, it is preferably methyl, ethyl, n-propyl, isopropyl or tert-butyl, alkenyl such as vinyl or 1,1-dimethyl-allyl or 2-fluoro-3-methyl-2-butenyl or alkynyl such as ethynyl or propynyl.

The compounds of formula I may possess a cyclopropane moiety of cis, trans structure, of cis structure, or of trans structure. The invention more particularly has as its object the compounds of formula I in which the cyclopropane moiety is of 1R, cis or 1R, trans structure.

Among the preferred compounds of formula I are those wherein R is either saturated or unsaturated straight-chain alkyl of 1 to 18 carbon atoms optionally substituted by at least one halogen or

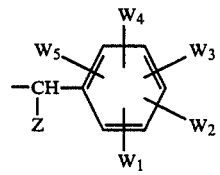

wherein Z is hydrogen, alkyl of 1 to 18 carbon atoms, alkenyl or alkynyl radical of 2 to 18 carbon atoms or cyano, $W_1$, $W_2$, $W_3$, $W_4$, $W_5$ are individually hydrogen, alkyl of 1 to 18 carbon atoms, alkenyl or alkynyl of 2 to 18 carbon atoms or cyano, —$CF_3$, —$NO_2$ or —O—$R_1'$, $R_1'$ is alkyl, alkenyl or alkynyl of up to 8 carbon atoms, halogen,

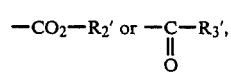

$R_2'$ and $R_3'$ are alkyl of 2 to 18 carbon atoms or

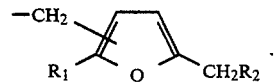

wherein $R_1$ is hydrogen or methyl and $R_2$ is a monocyclic aryl or —$CH_2$—C≡CH and especially 5-benzyl 3-furyl methyl or

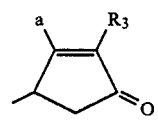

wherein a is hydrogen or methyl and $R_3$ is aliphatic organic of 2 to 6 carbon atoms and one or more carbon-carbon unsaturations especially —$CH_2$—CH=$CH_2$, —$CH_2$—CH=CH—$CH_3$, —$CH_2$—CH=CH—CH=$CH_2$, —$CH_2$—CH=CH—$CH_2$—$CH_3$, or —$CH_2$—C≡CH or

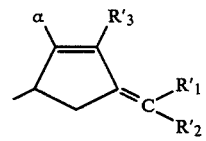

wherein a is hydrogen or methyl, $R_3$ has the above meaning, $R_1'$ and $R_2'$ are individually hydrogen, halogen, alkyl of 1 to 6 carbon atoms, aryl of 6 to 10 carbon atoms, alkyloxycarbonyl of 2 to 5 carbon atoms or cyano or

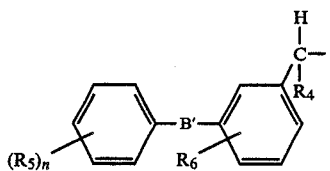

wherein B' is oxygen or sulfur,

or —CH$_2$— or sulfoxide or sulfone and R$_4$ is hydrogen, —C≡N, methyl, —CONH$_2$, —CSNH$_2$ or —C≡CH, R$_5$ and R$_6$ are individually hydrogen, halogen or methyl, and n is a whole number of 0, 1 or 2 and especially 3-phenoxybenzyl, α-cyano-3-phenoxy benzyl, α-ethynyl-3-phenoxy-benzyl, 3-benzoyl-benzyl, 1-(3-phenoxy-phenyl)-ethyl or α-thioamido-3-phenoxy-benzyl or

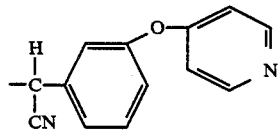

or

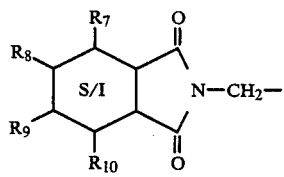

wherein R$_7$, R$_8$, R$_9$ and R$_{10}$ are hydrogen, chlorine or methyl and S/I symbolises an aromatic ring or an analogous dehydro or tetrahydro ring or

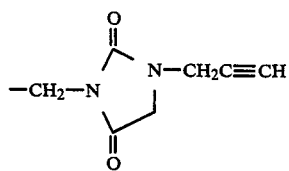

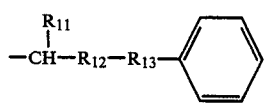

wherein R$_{11}$ is hydrogen or —CN, R$_{13}$ is —CH$_2$— or oxygen, R$_{12}$ is thiazolyl or thiadiazolyl wherein the attachment with

can occupy any of the available positions, R$_{13}$ is linked with R$_{12}$ by the carbon atom included between the sulfur atom and a nitrogen or

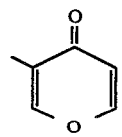

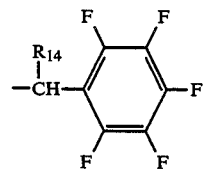

wherein R$_{14}$ is hydrogen or —CN, or ethynyl or

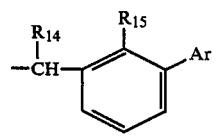

wherein R$_{14}$ is hydrogen, methyl, ethynyl or cyano and R$_{15}$ which is different from R$_{14}$ is hydrogen, fluorine or bromine, and Ar is aryl of 6 to 14 carbon atoms or

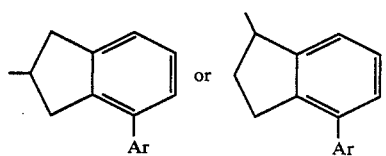

wherein Ar is aryl of 6 to 14 carbon atoms or

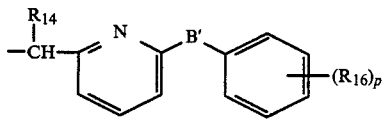

wherein R$_{14}$ is defined as above, each R$_{16}$ group is individually alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is a whole number of 0, 1 or 2 and B' is oxygen or sulfur or

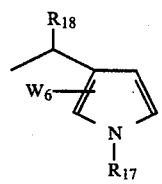

wherein R$_{17}$ is an unsaturated alkyl of 2 to 8 carbon atoms and W$_6$ is hydrogen, halogen, alkyl of 1 to 18 carbon atoms, aryl of 6 to 14 carbon atoms, aralkyl of 7 to 18 carbon atoms, cyano, CF$_3$, —CO$_2$—alkyl of 2 to 8 carbon atoms, —NO$_2$, or alkoxy of 1 to 8 carbon atoms, R$_{18}$ is hydrogen, —C≡N, methyl, —CONH$_2$, —CSNH$_2$ or —C≡CH.

Among the preferred possibilities for R are the following radials

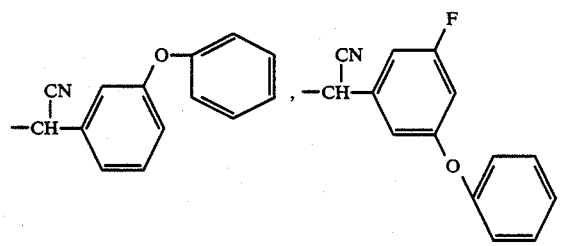

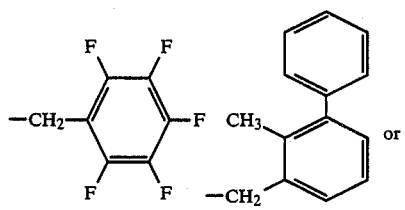

Preferably A is methyl and B is preferably hydrogen or methyl.

Specific preferred compounds of formula I are S-cyano-3-phenoxy-benzyl 1R cis 3-[ΔZ,(3 ΔZ, methoxyimino)-1-propenyl]2,2-dimethyl-cyclopropane carboxylate and S-cyano-(3-phenoxy-benzyl) 1R, cis 3-[ΔZ, (3 ΔE methoxyimino-1-propenyl]-2,2-dimethyl-cyclopropane carboxylate.

The novel process of the invention for the preparation of the compounds of formula I comprises reacting an acid of the formula

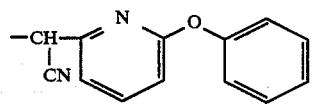

or a functional derivative thereof wherein A and B have the above definitions with an alcohol of the formula ROH in which R has the above definition to obtain the corresponding ester of formula I and, if desired, separating the various stereoisomers possibly obtained.

As the functional derivative of the acid, preferably the acid chloride or an acid anhydride is used. The esterification can be achieved according to classical esterification procedures, notably by esterification of the acid with the alcohol in the presence of a carbodiimide, with or without a base. The different stereoisomers can be separated by chromatography.

The products of formula II are new products and are themselves one of the objects of the invention and they can be obtained by reacting a compound of the formula

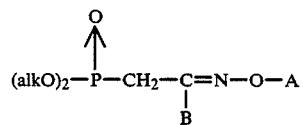

wherein A and B have the above definitions and alk is alkyl of 1 to 4 carbon atoms to a Wittig reaction in the presence of a strong base with an acid of the formula

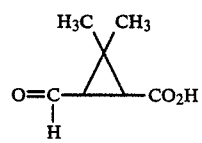

in its open form or its hemiacetal cyclized form (that is in the form of a lactone) or with a derivative of such an acid to obtain the corresponding compound of formula II.

The strong base used is preferably an alkali metal alcoholate for example sodium or potassium tert-butylate.

The phosphonates employed as starting materials are prepared according to the following reaction.

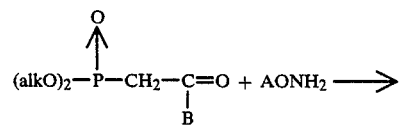

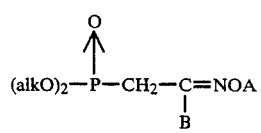

wherein A and B have the above definitions.

The compounds of formula I can equally be prepared by procedures equivalent to those described above, and thus one can first prepare the compound of the formula

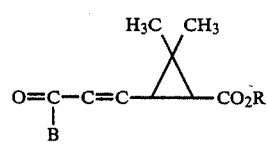

wherein B and R have the above definitions and react the latter with a compound of formula

AONH₂  VI wherein A has the above definition to obtain the corresponding compound of formula I The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

Certain of the compounds of formula I possess an excellent lethal power and a very good knock-down power and the products of Examples 1, 2, 3, 4, 7 and 8 are particularly remarkable on this point. The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 25% by weight, preferably.

In the case of a serpentine insecticide, the inert support may be made, for example, of pyrethrum marc, Tabu powder or (Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 25% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)bicyclo-[2,2,1] 5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene-methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxybenzyl alcohol with 2-p-chlorophenyl-2-isopropyl-acetic acids, esters of allethrolone, 3,4,5,6-tetrahydrophthalimido-methyl alcohol, 5-benzyl-3-furylmethyl alcohol, 3-phenoxy-benzyl alcohol or α-cyano- 3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

S-cyano-3-phenoxy-benzyl 1R trans 3-[ΔZ 3-(ΔZ methoxyimino)-1-butenyl]-2,2-dimethyl-cyclopropane carboxylate and the corresponding 3-[ΔZ, 3-(ΔE, methoxyimino)-1-butenyl], 3-[ΔE, 3-(ΔE, methoxyimino)-1-butenyl] and 3-[ΔE 3-[ΔZ methoxy-imino)-1-butenyl]-isomers A solution of 11.4 g of 1R trans 3-[3-methoxyimino-1-butenyl]-2,2-dimethylcyclopropane carboxylic acid (mixture of the 4 E and Z isomers at the double bonds), 11.55 g of S-phenocyanol, 120 mg of 4-dimethylaminopyridine and 60 ml of methylene chloride was cooled to 0° C. and 12.2 g of dicyclohexylcarbodiimide and 60 ml of methylene chloride were introduced at 0° C. The solution was allowed to return to ambient temperature and was filtered. After evaporation of the solvent, 25 g of crude product were obtained which was chromatographed successively over silica eluting with an MeOt-Bu-hexane mixture (2-8), then over silica eluting with a chloroform-hexane-isopropyl ether mixture (2-7-1) to obtain the desired 4 isomers.

EXAMPLE 2

S-cyano-3-phenoxy-benzyl 1R cis 3-[ΔE, 3-(ΔE methoxyimino)-1-butenyl]-2,2-dimethylcyclo-propane carboxylate and the corresponding 3-[ΔE, 3-(ΔZ methoxyimino)-1-butenyl], 3-[ΔZ, 3-(ΔE methoxyimino)-1-butenyl] and 3-[ΔZ 3-(ΔZ methoxyimino)-1-butenyl] isomers Using the procedure of Example 1, 1R cis 3-[3-methoxyimino-1-butenyl]-2,2-dimethylcyclopropane carboxylic acid (mixture of the 4 E and Z isomers at the position of the two double bonds) and S-phenocyanol were reacted to obtain the 4 isomers sought with the following specific rotations.

ΔE, ΔE isomer $[\alpha]_D = +23.5° \pm 1°$ (c=0.8% in CHCl$_3$).

ΔE, ΔZ isomer $[\alpha]_D = +24.5° \pm 2°$ (c=0.5% in CHCl$_3$).

ΔZ, {E isomer $[\alpha]_D = +73° \pm 1.5°$ (c=1.2% in CHCl$_3$).

EXAMPLE 3

S-cyano-3-phenoxy-benzyl 1R, trans 3-[ΔE, 3-(ΔE-methoxyimino-1-propenyl)]-2,2-dimethylcyclopropane carboxylate, and A and B isomers at the imino position Using the procedure of Example 1, the corresponding acid was reacted to obtain the following isomers.
A isomer: $[\alpha]_D = -3° \pm 1.5°$ (c=0.7% in CHCl$_3$).
B isomer: $[\alpha]_D = -22.5° \pm 2°$ (c=0.5% in CHCl$_3$).

EXAMPLE 4

S-cyano-3-phenoxy-benzyl 1R, cis 3-[ΔE, 3-(ΔE methoxyimino)-1-propenyl]-2,2-dimethylcyclopropane carboxylate and the corresponding 3-[ΔE, 3-(ΔZ methoxyimino)-1-propenyl], 3-[ΔZ, 3-(ΔZ methoxyimino)-1-propenyl] and '-[ΔZ, 3-(ΔE methoxyimino)-1-propenyl]-isomers Using the procedure of Example 1, 1R cis [3-methoxyimino-1-propenyl]-2,2-dimethylcyclopropane carboxylic acid and S-phenocyanol were reacted to obtain the sought products and the ΔE, ΔE isomer melted at 70° C.

EXAMPLE 5

S-cyano-3-phenoxy-4-fluorobenzyl 1R, cis 3-[ΔZ, 3-(ΔE methoxyimino)-1-propenyl]-2,2-dimethylcyclopropane carboxylate and the corresponding ΔZ, ΔZ isomer Using the procedure of Example 1, 1R, cis 3-[methoxyimino-1-propenyl]-2,2-dimethylcyclopropane carboxylic acid (mixture of isomers) and Sα-cyano-3-phenoxy-4-fluorobenzyl alcohol were reacted to obtain the products sought.

EXAMPLE 6

(pentafluorophenyl)-methyl 1R, cis 3-[ΔZ, 3-(ΔE methoxyimino)-1-propenyl]-2,2-dimethylcyclopropane carboxylate and the corresponding 3-(ΔZ, 3-(ΔZ methoxyimino)-1-propenyl] isomer Using the procedure of Example 1, 1R, cis 3-[methoxyimino-1-propenyl]-2,2-dimethylcyclopropane carboxylic acid (mixture of isomers) was reacted to obtain the products sought.
ΔZ, ΔE isomer melted at 51° C. and
ΔZ, ΔZ isomer melted at 72° C.

EXAMPLE 7

2-methyl-3-phenyl-benzyl 1R, cis 3-[ΔZ, 3-(ΔE methoxyimino)-1-propenyl]-2,2-dimethylcyclopropane carboxylate and the corresponding ΔZ, ΔZ isomer Using the procedure of Example 1, 1R, cis 3-[3-methoxyimino-1-propenyl]-2,2-dimethylcyclopropane carboxylic acid (mixture of isomers) and (2-methyl-3-phenyl-phenyl)-methyl alcohol were reacted to obtain the products sought.

EXAMPLE 8

RS cyano-1-(6-phenoxy-2-pyridyl)-methyl 1R, cis 3-[ΔZ, 3-(ΔE methoxyimino)-1-propenyl]-2,2-dimethylcyclopropane carboxylate and the corresponding ΔZ, ΔZ isomer Using the procedure of Example 1 1R, cis 3-[methoxyimino-1-propenyl]-2,2-dimethylcyclopropane carboxylic acid and RS-cyano-1-(6-phenoxy-2-pyridyl-methyl alcohol were reacted to obtain the products sought.

EXAMPLE 9

(pentafluorophenyl)-methyl 1R, cis 3-[ΔE, 3-(ΔE methoxyimino)-1-propenyl]-2,2-dimethylcyclopropane carboxylate and the corresponding 3-[ΔE, 3-(ΔZ methoxyimino)-1-propenyl] isomer 1.35 g of hydroxylamine hydrochloride, 20 ml of water, 5 ml of dioxane and 1.25 ml of pyridine were mixed for 30 minutes at ambient temperature and the mixture was cooled to +5° C. and 4 g of (pentafluorophenyl)-methyl 1R, cis 2,2-dimethyl-3-[3-oxo-1-propenyl]-cyclopropane carboxylate in 30 ml of dioxane were added and the reaction medium was allowed to return to 20° C., then diluted with 20 ml of water and extracted with ethyl acetate. The organic phases were dried and the solvent was eliminated under reduced pressure to obtain 4.4 g of crude product which was chromatographed over silica (eluent: hexane-isopropyl ether 96-4) to obtain 2.85 g of the expected ΔE, ΔE isomer and 0.85 g of the expected ΔE, ΔZ isomer

| Analysis: $C_{17}H_{16}F_5NO_3$: molecular weight = 377.215 | | | | |
|---|---|---|---|---|
| Calculated: | % C 54.13 | % H 4.28 | % N 3.71 | % F 25.18 |
| ΔE, ΔE isomer found: | 54.3 | 4.2 | 3.6 | 25.1 |
| ΔE, ΔZ isomer found: | 54.4 | 4.3 | 3.6 | 24.9 |

ΔE, ΔE isomer $[\alpha]_D = -41.5° \pm 1.5°$ (c = 1% in CHCl$_3$)
ΔE, ΔZ isomer $[\alpha]_D = -6° \pm 1°$ (c = 1% in CHCl$_3$)

EXAMPLE 10

Tetrafluoro-4-methyl-benzyl 1R, cis 3-[ΔZ, 3-(ΔE methoxyimino)-1-propenyl]-2,2-dimethylcyclopropane carboxylate and the corresponding 3-[ΔE, 3-(ΔE methoxyimino)-1-propenyl], 3-[ΔZ, 3-(ΔZ methoxyimino)-1-propenyl] and 3-[ΔE, 3-(ΔZ methoxyimino)-1-propenyl] isomers Using the procedure of Example 1, 5.4 g of tetrafluoro-4-methyl-benzyl 1R, cis 2,2-dimethyl-3-[3-oxo-1-propenyl]-cyclopropane carboxylate was reacted and two successive chromatographies were effected. The first chromatography over silica (eluent: cyclohexane-isopropyl ether 92.5-7.5) yielded 0.66 g of ΔZ, ΔE isomer and 1.4 g of ΔE, ΔE isomer and 0.8 g of a mixture which was chromatographed over silica (eluent: methylene chloride-heptane 7-3) to obtain 0.25 g of ΔZ, ΔZ isomer and 0.34 g of ΔE, ΔZ isomer.

| Analysis: $C_{18}H_{19}F_4NO_3$: molecular weight = 373.351 | | | | |
|---|---|---|---|---|
| Calculated: | % C 57.91 | % H 5.13 | % N 3.75 | % F 20.35 |
| ΔZ, ΔE isomer found: | 57.8 | 5.1 | 3.8 | 20.7 |
| ΔE, ΔE isomer found: | 57.7 | 5.2 | 3.8 | 20.3 |
| ΔZ, ΔZ isomer found: | 57.7 | 5.1 | 3.7 | 20.5 |
| ΔE, ΔZ isomer found: | 57.6 | 5.1 | 3.7 | 20.2 |

ΔZ, ΔE isomer $[\alpha]_D = +43° \pm 2.5°$ (c = 0.5% in CHCl$_3$)
ΔE, ΔE isomer $[\alpha]_D = -53.5° \pm 1.5°$ (c = 1.6% in CHCl$_3$)
ΔZ, ΔZ isomer $[\alpha]_D = +8° \pm 1°$ (c = 1.2% in CHCl$_3$)
ΔE, ΔZ isomer $[\alpha]_D = -20° \pm 2°$ (c = 0.65% in CHCl$_3$)

PREPARATION 1

1R, trans 3-[ΔE, ΔZ, 3-(ΔE, ΔZ methoxyimino)-1-propenyl]-2,2-dimethylcyclopropane carboxylic acid 1.25 g of potassium tert-butylate were introduced at −60° C. into a solution of 1 g of dimethyl-2-methoxyiminoethyl phosphonate, 0.75 g of 1R, trans 2,2-dimethyl-3-formyl-cyclopropane carboxylic acid and 20 ml of tetrahydrofuran and the solution was stirred for 1 hour at −60° C. and an N aqueous solution of hydrochloric acid was added. Extraction was carried out with ethyl acetate, and the extracts were dried and evaporated to dryness to obtain 1.1 g of 1R, trans 3-[ΔE, ΔZ, 3-(ΔE, ΔZ methoxyimino)-1-propenyl]-2,2-dimethylcyclopropane carboxylic acid.

Dimethyl 2-methoxyiminoethyl phosphonate used at the start of the preparation was prepared as follows:

32.2 g of 0-methylhydroxylamine hydrochloride, 90 ml of water and 540 ml of dioxane were added to a solution containing 45 g of

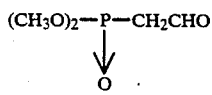

phosphonic aldehyde and 55 ml of pyridine and the mixture was stirred at ambient temperature for 3 hours, then evaporated to dryness. 40 ml of an N aqueous hydrochloric acid solution were added and extraction was carried out with dichloromethane. The extracts were dried and evaporated under reduced pressure to obtain 46 g of crude product which was chromatographed over silica (eluent: $CH_2Cl_2$ AcOET 1/1) to obtain 17.7 g of dimethyl 2-methoxyiminoethyl phosphonate.

PREPARATION 2

1R, cis 3-[ΔE, ΔZ, 3-(ΔE, ΔZ methoxyimino)-1-propenyl]-2,2-dimethylcyclopropane carboxylic acid Using the procedure of Example 1, dimethyl methoxyiminoethyl phosphonate and the lactone of 2,2-dimethyl-3-formylcyclopropane carboxylic acid were reacted to obtain 1R, cis 3-[ΔE, ΔZ, 3-(ΔE, ΔZ methoxyimino)-1-propenyl]-2,2-dimethylcyclopropane carboxylic acid.

PREPARATION 3

1R, cis 3-[ΔE, ΔZ, 3-(ΔE, ΔZ methoxyimino)-1-butenyl]-2,2-dimethylcyclopropane carboxylic acid Using the procedure of preparation 1, dimethyl-2-methoxyiminopropyl-phosphonate and the lactone of 2,2-dimethyl-3-formylcyclopropane carboxylic acid were reacted to obtain 1R, cis 3-[ΔE, ΔZ, 3-(ΔE, ΔZ methoxy imino)-1-butenyl]-2,2-dimethylcyclopropane carboxylic acid.

The starting product, namely dimethyl 2-methoxyiminopropyl phosphate was prepared as follows:

14.5 g of methyldroxylamine hydrochloride and 40 ml of water were added at 15° C. to a solution of 22.2 g of

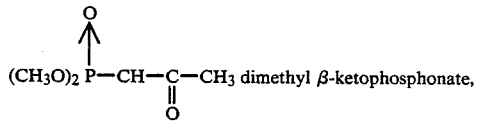
dimethyl β-ketophosphonate, 25 ml of pyridine and 235 ml of dioxane followed by stirring for one hour at ambient temperature, followed by evaporation to dryness. 250 ml of an iced N aqueous solution of hydrochloric acid and 250 ml of methylene chloride were added and after decanting, the aqueous phase was extracted with methylene chloride. The organic phases were dried and evaporated under reduced pressure to obtain 24.8 g of crude product which was chromatographed over silica eluting with a methylene chloride-acetone mixture (1/1) to obtain 20.8 g of the product sought.

PREPARATION 4

1R, trans 3-[ΔE, ΔZ, 3-(ΔE, ΔZ methoxyimino)-1-butenyl]-2,2-dimethylcyclopropane carboxylic acid Using the procedure of preparation 1, dimethyl-2-methoxyiminopropyl-phosphonate and 1R, trans 2,2-dimethyl-3-formylcyclopropane carboxylic acid were reacted to obtain 1R, trans 3-[ΔE, ΔZ, 3-(ΔE, ΔZ methoxyimino)-1-butenyl]-2,2-dimethylcyclopropane carboxylic acid.

PREPARATION 5 tetrafluoro-4-methyl-benzyl) 1R, cis 2,2-dimethyl-3-[3-oxo-1-propenyl]-cyclopropane carboxylate A suspension of 12.85 g of methyl 1R, cis 2,2-dimethyl-3-formylcyclopropane carboxylate and 70.6 g of (1,3-dioxolan-2-yl]-methyltriphenyl phosphonium bromide was cooled to −50° C. and then 18.5 g of potassium tertbutylate in 260 ml of tetrahydrofuran were added over one hour. The resulting mixture was stirred for one hour at −50° C., poured onto iced water and extracted with isopropyl ether. The extracts were dried and the solvent was eliminated under reduced pressure. The result was taken up in isopropyl ether and phospine oxide was eliminated by filtration. The filtrates were evaporated to dryness and the residue was subjected to chromatography on silica (eluent: ether-hexane 3-7) to obtain 12.45 g of the expected product. 3.8 g of the said ester in 60 ml of methanol and 20 ml of N sodium hydroxide were refluxed for one and a half hours and the methanol was eliminated under reduced pressure. Extraction was carried out with methylene chloride and the extracts were washed. The combined aqueous phases were cooled to +5° C. and 3.1 g of monosodic phosphate in solution in 30 ml of water were added slowly. Sodium chloride was added and extraction was done with methylene chloride. The extracts were dried and the solvent was partially evaporated under reduced pressure at 25° C. 2.6 g of tetrafluoro-4-methyl-benzyl alcohol and 35 mg of 4-dimethylamino-pyridine were added and the solution was cooled to 0° C. 3.5 g of dicyclohexycarbodiimide in 20 ml of methylene chloride were added slowly and was followed by stirring for 16 hours at 0° C. The dicyclohexylurea was eliminated by filtration and then the solvent was evaporated at 20° C. under reduced pressure. The residue was taken up in 55 ml of acetone and 15 ml of water and the solution was cooled. 340 mg of p-toluene sulfonic acid were added and the mixture was stirred for 75 minutes at 0° C., neutralized with sodium bicarbonate, then extracted with isopropyl ether. The solvent was eliminated under reduced pressure at 25° C. to obtain 5.4 g of tetrafluoro-4-methylbenzyl 1R, cis 2,2-dimethyl-3-[3-oxo-1-propenyl]-cyclopropane carboxylate.

PREPARATION 6

Pentafluorobenzyl 1R, cis 2,2-dimethyl-3-[3-oxo-1-propenyl]cyclopropane carboxylate Using the procedure of preparation 5, pentafluorophenylmethyl alcohol was reacted to obtain pentafluorobenzyl 1R, cis 2,2-dimethyl-3-[3-oxo-1-propenyl]-cyclopropane carboxylate.

EXAMPLE 11

Preparation of a soluble concentrate was prepared as a homogeneous mixture of 0.25 g of the product of Example 4, ΔZ, ΔZ isomer, 1.00 g of Piperonyl butoxide, 0.25 g of Tween 80, 0.1 g of Topanol A and 98.4 g of water.

EXAMPLE 12

Preparation of an emulsifiable concentrate was obtained by throughly mixing 0.015 g of the product of Example 4 ΔZ (C=C) ΔE (C=N), 0.5 g of Piperonyl butoxide, 0.1 g of Topanol A, 3.5 g of Tween 80 and 95.885 g of Xylene.

EXAMPLE 13

Preparation of an emulsifiable concentrate was prepared by homogeneously mixing 1.5 g of the product of Example 4 ΔZ, ΔZ isomer, 20.0 g of Tween 80, 0.1 g of Topanol A and 78.4 g of Xylene.

EXAMPLE 14

Preparation of a fumigenic composition was prepared by homogeneously mixing 0.25 g of the product of Example 1, ΔE, ΔE isomer, 25.00 g of Tabu powder, 40.0 g of Cedar leaf powder, 33.75 g of Pinewood dust, 0.5 g of Brilliant Green and 0.5 g of p-nitrophenol.

BIOLOGICAL STUDY OF THE COMPOUNDS OF THE INVENTION (A) Study of the knockdown effect on the domestic fly The insects tested were female domestic flies 4 days old. The test was done by direct pulverization at a concentration of 0.1 g/l in a Kearns and March chamber, using as solvent a mixture of axetone (5%) and of Isopar L (petroleum solvent) (quantity of solvent used 2 ml per second). 50 insects per treatment were used and checks were carried out every minute up to 10 minutes and then at 15 minutes and the $KT_{50}$ was determined by the usual methods. The experimental results obtained are summarized in the following Table.

| Compounds | C=N | C=C | KT 50 in mn |
|---|---|---|---|
| Example 1 | Z | Z | 5.1 |
| Example 1 | E | Z | 2.48 |
| Example 2 | Z | Z | 3.5 |
| Example 4 | E | Z | 3.1 |
| Example 5 | E | Z | 3.1 |
| Example 5 | Z | Z | 3.4 |
| Example 6 | Z | E | 6.7 |
| Example 6 | Z | Z | 5.9 |

Conclusion: The products show a very useful knockdown power.

(B) Study of the lethal effect on larvae of *Spodoptera littoralis*

The tests were carried out by topical application of an acetone solution by an Arnold micro manipulator on the dorsal thorax of the larvae and 15 larvae were used per dose of product under test. The larvae used were larvae of the fourth larval stage, that is about 10 days old, when they were bred at 24° C. and 65% relative humidity. After treatment, the individuals were placed on an artificial nutritive medium (Poitout medium) and a check of the mortalities 48 hours after treatment was carried out. The experimental results obtained were summarized in the following Table.

| Compounds | C=N | C=C | LD 50 in ng |
| --- | --- | --- | --- |
| Example 2 | Z | E | 6.4 |
| Example 4 | E | Z | 1.3 |
| Example 4 | Z | Z | 2.5 |
| Example 5 | E | Z | 7.7 |

Conclusion: The products show a good activity in this test.

Various modifications of the products and methods of the invention may be made without departing from the spirit or scope thereof and it is to be understood that the invention is intended to be limited only as defined in the appended claims.

What we claim is:

1. All possible stereoisomeric forms and mixtures thereof of a compound of the formula

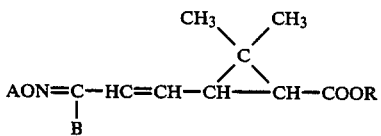

wherein A is selected from the group consisting of hydrogen, alkyl of 1 to 18 carbon atoms and alkenyl of 2 to 18 carbon atoms unsubstituted or substituted with one halogen, B is selected from the group consisting of hydrogen and methyl and R is selected from the group consisting of

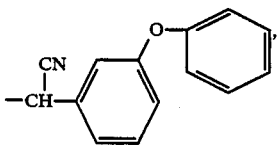

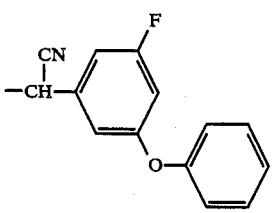

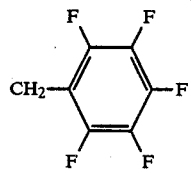

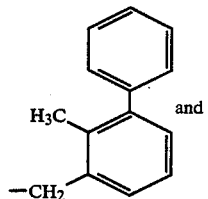

and

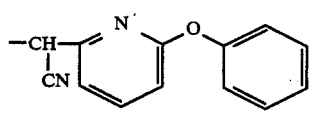

2. A compound of claim 1 wherein the cyclopropane moiety has the 1R, cis or 1R, trans structure.
3. A compound of claim 1 wherein A is methyl.
4. A compound of claim 1 wherein B is hydrogen.
5. A compound of claim 1 wherein B is methyl.
6. A compound selected from the group consisting of S-cyano-3-phenoxy-benzyl 1R, cis 3-ΔZ, (3-ΔZ, methoxyimino)-1-propenyl]-2,2-dimethylcyclopropane carboxylate and S-cyano 3-phenoxy-benzyl 1R, cis 3-[ΔZ, (3-ΔE methoxyimino)-1-propenyl]-2,2-dimethylcyclopropane carboxylate.
7. An insecticidal composition comprising an insecticidally effective amount of a compound of claim 1 and an inert carrier.
8. A composition of claim 7 wherein the cyclopropane moiety has the 1R, cis or 1R, trans structure.
9. A composition of claim 7 wherein A is methyl.
10. A composition of claim 7 wherein B is hydrogen.
11. A composition of claim 7 wherein B is methyl.
12. A composition of claim 7 wherein the compound is selected from the group consisting of S-cyano-3-phenoxy-benzyl 1R, cis 3-[ΔZ, (3-ΔZ, methoxyimino)-1-propenyl]-2,2-dimethylcyclopropane carboxylate and S-cyano-3-phenoxy-benzyl 1R, cis 3-[ΔZ, (3-ΔE methoxyimino)-1-propenyl]-2,2-dimethylcyclopropane carboxylate.
13. A method of combatting insects comprising contacting insects with an insecticidally effective amount of a compound of claim 1.
14. A method of claim 13 wherein the cyclopropane moiety has the 1R, cis or 1R, trans structure.
15. A method of claim 13 wherein A is methyl.
16. A method of claim 13 wherein B is hydrogen.
17. A method of claim 13 wherein B is methyl.
18. A method of claim 13 wherein the compound is selected from the group consisting of S-cyano 3-phenoxy-benzyl 1R, cis 3-[ΔZ, (3-ΔZ, methoxyimino)-1-propenyl]-2,2-dimethylcyclopropane carboxylate and S-cyano 3-phenoxy-benzyl 1R, cis 3-[ΔZ, (3-ΔE methoxyimino)-1-propenyl]-2,2-dimethylcyclopropane carboxylate.

* * * * *